United States Patent [19]

Millet

[11] 4,198,973
[45] Apr. 22, 1980

[54] INTRAVENOUS CATHETER ASSEMBLY WITH FLUID FLOW RESTRICTION CAPABILITY

[75] Inventor: Marcus J. Millet, New York, N.Y.

[73] Assignee: Johnson & Johnson, New Brunswick, N.J.

[21] Appl. No.: 944,045

[22] Filed: Sep. 20, 1978

Related U.S. Application Data

[63] Continuation-in-part of Ser. No. 886,498, Mar. 14, 1978.

[51] Int. Cl.² ............................................... A61M 5/00
[52] U.S. Cl. .......................... 128/214.4; 128/DIG. 16
[58] Field of Search ................ 128/214 R, 214.4, 348, 128/347, DIG. 16

[56] References Cited

U.S. PATENT DOCUMENTS

| | | | |
|---|---|---|---|
| 3,472,232 | 10/1969 | Earl | 128/214.4 X |
| 3,537,451 | 11/1970 | Beck et al. | 128/214.4 |
| 3,906,946 | 9/1975 | Nordstrom | 128/214.4 |
| 4,006,744 | 2/1977 | Steer | 128/214 R |

OTHER PUBLICATIONS

Deseret Company Brochure, May 1978—ANGI-O-SET® description, Sandy, Utah.

*Primary Examiner*—Dalton L. Truluck

[57] ABSTRACT

An intravenous catheter assembly for use in the administration of fluids to a patient includes a compressible, flexible hub having a bore therethrough. One end of the bore is adapted to receive a hollow tube such as an intravenous catheter so that fluid is flowable through the bore and the tube. A pair of generally oppositely extending wing sections is connected to the hub, at least one of the wings being hingedly connected to the hub to allow that wing to fold over the hub. On the hingedly connected wing is a pinching protuberance for contact with the hub when the wing is folded thereover whereby, in use, the folded wing urges the protuberance against the flexible hub causing it to collapse and occlude the bore and thereby restrict fluid from passing therethrough.

1 Claim, 6 Drawing Figures

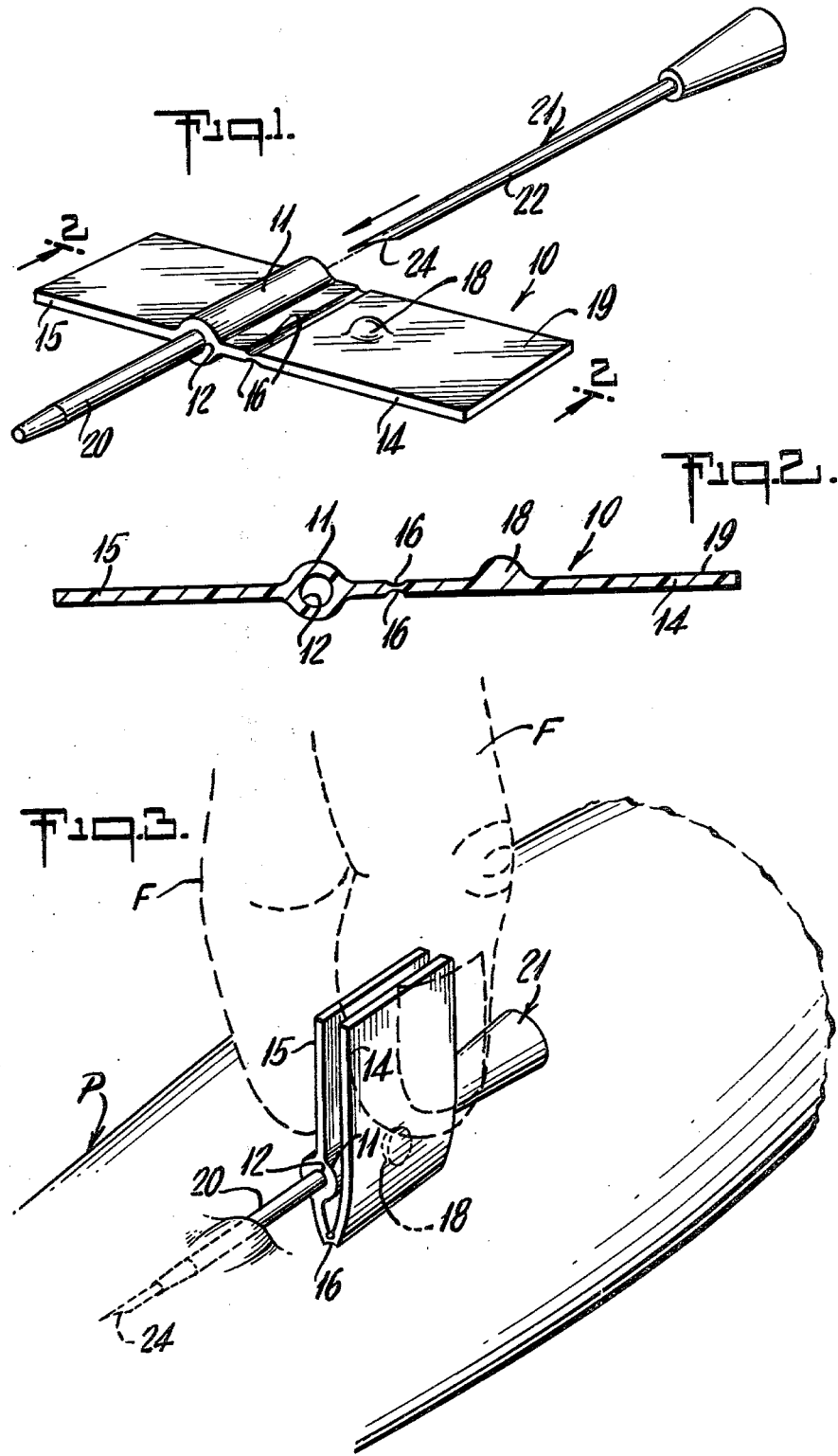

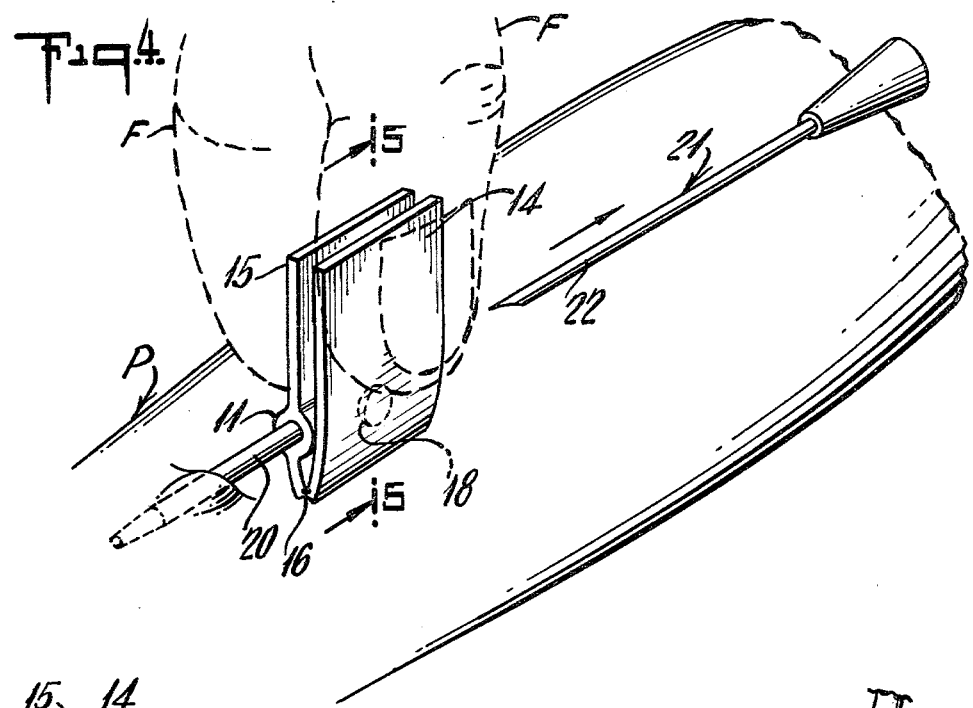
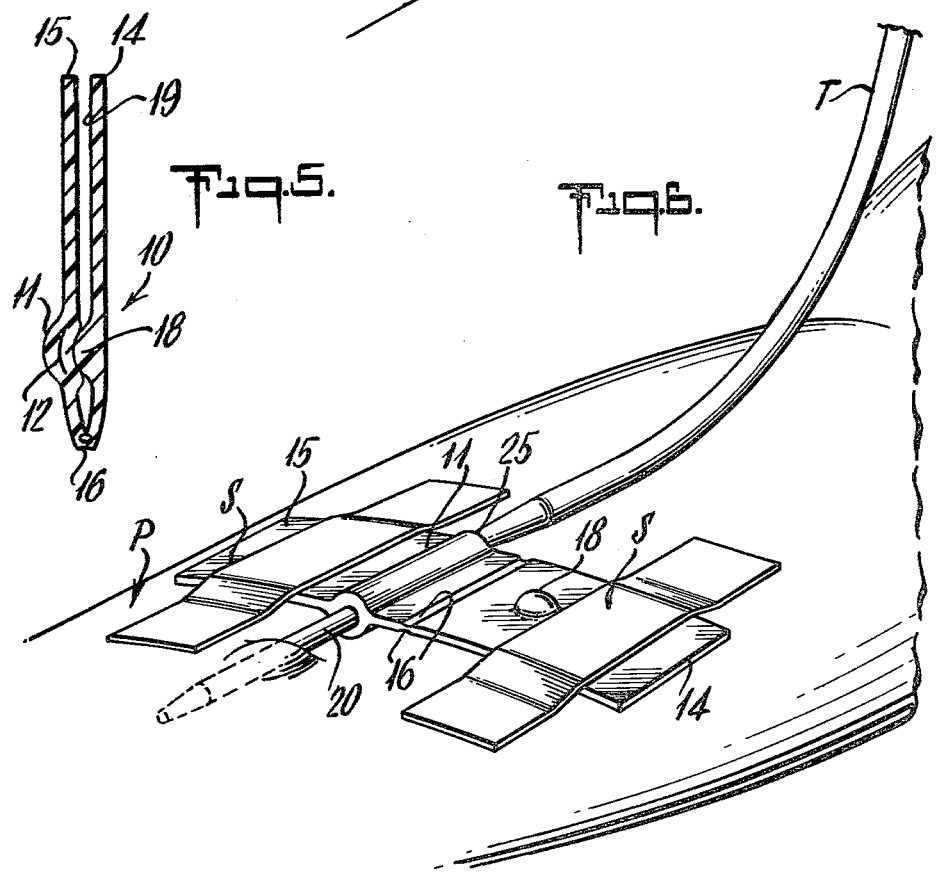

INTRAVENOUS CATHETER ASSEMBLY WITH FLUID FLOW RESTRICTION CAPABILITY

BACKGROUND OF THE INVENTION

This application is a continuation-in-part application of application Ser. No. 886,498, filed Mar. 14, 1978.

This invention relates to an intravenous catheter assembly, and more particularly concerns an intravenous catheter assembly which has the capability for the user to manipulate the same to restrict fluid from passing therethrough.

Many intravenous catheters which are employed to deliver intravenous solution to a patient are initially inserted into that patient's vein in combination with an introducer needle. Generally, the needle is a sharp-pointed cannula which fits inside the catheter. Both are inserted into the patient's vein, the sharp point of the needle leading the way. After the combined catheter and needle are in position, the needle is withdrawn and the intravenous infusion set or other appropriate device is connected to the hub end of the catheter for delivering fluid to the patient. Before the infusion set hook-up is connected, however, there may be a problem of blood flowing out of the intravenous tubing after the needle has been removed, inasmuch as one end of the catheter remains inserted in the patient's vein. Most of the prior efforts to prevent outflow of blood from the intravenous catheter have been made by sealing its back end with an elastomeric seal of some type, and then inserting the cannula of the needle through the seal and into its position into the catheter. These devices have been prone to failure because of the tendency for the elastomeric seal to take a set during storage. The alternative of inserting the introducer cannula through the elastomeric seal immediately before the device is to be used is extremely inconvenient.

Various wing-type cannula devices have been proposed which provide a fluid-tight fit of a catheter tubing which has been inserted therein. For instance, in U.S. Pat. No. 4,006,744 a cannula mount is provided with an intermediate length of flexible tubing which is compressed around the catheter tubing after being inserted therein in order to provide a fluid-type fit. To produce this fit, a hinged jaw is closed onto another jaw to clamp the cannula portion inside the flexible tubing. Other holders for tubular items such as injection cannulae are disclosed in U.S. Pat. Nos. 3,834,380; 3,589,361; and 3,472,232. In these references, wing portions of the particular devices are employed to clamp or hold the tubular item in place, e.g., after venipuncture has occurred. While the inventions disclosed in these references provide a fluid tight seal between a catheter and a flexible holder, they are silent as to the prevention of fluid from flowing through the clamped catheter or tube. In other words, even by employing the devices disclosed by these references and other devices known in the art, the problem of blood flowing out from the catheter, especially immediately after the needle has been removed, has remained unsolved.

SUMMARY OF THE INVENTION

The intravenous catheter assembly of the present invention includes a compressible hub having a bore therethrough. One end of the bore is adapted to receive a hollow tube whereby fluid is flowable through the bore and the tube. A generally laterally extending section is connected to the hub and adapted to fold over the hub. This section includes means thereon for contact with the hub when that section is folded thereover whereby, in use, the section urges the contacting means against the hub causing it to collapse and occlude the bore and thereby restrict fluid from passing therethrough.

In the preferred embodiment of the intravenous catheter of the present invention, a hollow catheter has one of its ends connected to the bore for fluid passage through the bore and the catheter. A pair of generally oppositely extending, flexible wing sections is integrally formed with and connected to the hub, this integrally formed component being preferably fabricated from a flexible plastic material. One of the wings is hingedly connected to the hub by means of a weakened portion of material adjacent the hub to allow that wing to fold over the hub. Protuberative pinching means is included on the surface of the hingedly connected wing for contact with the hub when the wing is folded over. In use, the folded wing urges the protuberative pinching means against the hub causing the same to collapse and thereby restrict fluid flow in the bore.

The catheter assembly of the present invention is notably different from other catheter assemblies specifically of the wing-type construction. Particularly, the structure of the present invention allows the wing sections to be used to facilitate securement of the catheter assembly to the patient, while additionally providing a feature which allows the wings to operate in valve-like fashion to restrict the undesirable flow of fluids therethrough. Most advantageously, the valve-like feature is readily employed by the user of the present catheter assembly when a needle is withdrawn so that no blood will flow out of the catheter which remains inserted in the patient's vein. Besides overcoming this undesirable outflow of blood, the present invention is functionally convenient for its users.

BRIEF DESCRIPTION OF THE DRAWINGS

FIG. 1 is a perspective view illustrating the preferred catheter assembly of the present invention with a needle ready for insertion therein;

FIG. 2 is an enlarged cross-sectional view taken along line 2—2 of FIG. 1;

FIG. 3 is a perspective view of the preferred catheter assembly illustrating the folded wing section while the needle is still in position;

FIG. 4 is a perspective view of the preferred catheter assembly illustrating the valve-like action of the wing sections to restrict fluid flow after the needle has been removed;

FIG. 5 is an enlarged cross-sectional view taken along line 5—5 of FIG. 4; and

FIG. 6 is a perspective view illustrating the preferred catheter assembly secured to the patient with the intravenous fluid supply attached thereto.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly FIGS. 1 and 2, there is illustrated the preferred embodiment of the intravenous catheter assembly 10 of the present invention. Catheter assembly 10 includes a center portion or hub 11 through which extends a bore 12. Hub 11 is somewhat bulbous shaped in this instance so that its wall portion surrounding bore 12 is substantially the same thickness. In addition, hub 11 is fabricated from a compressible, flexible material which allows its walls to collapse sufficiently to occlude bore 12 under squeezing pressure. Integrally connected to and formed with hub 11 is a pair of generally oppositely extending, flexible wing sections 14 and 15. In other words, hub 11 and wings 14 and 15 form a unitary structure, such as is produced by molding and the like. Plastic materials which impart flexibility to the final molded structure are suitably employed to fabricate the hub and wing structure.

Wing 14 is adapted to fold over hub 11; to this end, a weakened portion, such as grooves 16 adjacent hub 11 and running substantially parallel thereto, serves as a flexible joint or a hinged connection to allow wing 14 to be folded. A protuberance 18 is included on the top surface 19 of wing 14. Protuberance 18 is, in this instance, a rounded projection or bump on surface 19 which is conveniently integrally formed on that surface of the wing. As seen especially in FIG. 2, protuberance 18 is spaced from grooves 16 so that when wing 14 is folded over hub 11, protuberance 18 is aligned for contact with hub 11. In this manner, protuberance 18 serves as a pinching device to collapse the wall of hub 11 into bore 12 to occlude the latter, as more clearly illustrated and explained hereinafter.

In one end of bore 12 a hollow catheter 20 is inserted. Catheter 20 is inserted only a short distance into bore 12 to make a tight connection so that fluid may flow through bore 12 and into catheter 20 on its way to the patient. Of course, there may be alternative embodiments wherein catheter 20 is inserted all the way through bore 12; in that case, catheter 20 must also be collapsible, at least that portion which lies inside bore 12, so that, under pinching pressure, the opening inside catheter 20 can be occluded to restrict fluid flow. Catheter assembly 10 may be conveniently used with a needle 21. A sharp pointed cannula 22, as part of needle 21, is adapted to slide through bore 12 and into hollow catheter 20 so that point 24 emerges beyond the tip of the catheter. In combination, both needle and catheter assembly are inserted into a vein of a patient P, with sharp point 24 of cannula 22 leading the way. It is pointed out that both cannula 22 and catheter 20 are actually inserted into the vein of the patient. This venipuncture is in preparation for the delivery of, for example, an intravenous solution to the patient and is illustrated in FIG. 3. As seen therein, wing 14 has been folded over hub 11 by means of the flexible hinge at grooves 16. The fingers F of the user grasp wings 14 and 15 which lie in a folded position with respect to each other in order to perform the venipuncture insertion of the assembly with the needle. At this stage, the catheter assembly of the present invention also provides an advantageous function. In the folded position, protuberance 18 contacts flexible hub 11 and compresses its wall into tight engagement with cannula 22. If any blood from the patient's vein should travel in the space between cannula 22 and the hollow opening of catheter 20, once that blood enters bore 12, it is restricted from flowing out of hub 11 because of the pinching action of hub 11 against cannula 22. Furthermore, the tight engagement of the hub wall against the needle when the wings are folded toward each other provides another advantageous feature. This tight engagement prevents the needle from moving or slipping backwards during the venipuncture insertion. Since point 24 of the needle extends out a short distance beyond the distal end of catheter 20 any backward movement of the needle along its longitudinal axis relative to the catheter would cause the sharp point to retract inside the catheter thereby preventing proper and comfortable venipuncture. However, the structure of the present invention in affording tight engagement between the hub wall and the needle when the wings are folded toward each other has accounted for and overcome this potential needle movement problem. Accordingly, the folding action of wings 14 and 15 toward each other, in conjunction with flexible, compressible hub 11, provides the two-fold advantage of preventing needle movement relative to the catheter during venipuncture insertion and preventing blood from passing through the annular space between the needle and the catheter.

Turning to FIGS. 4 and 5, catheter assembly 10 is illustrated in its operative condition after venipuncture has been made and after needle 21 has been withdrawn. As seen therein, wing 14 remains in its folded position with respect to hub 11 and wing 15 under the grasp of fingers F. The user gently and carefully withdraws needle 21 from bore 12 and catheter 20. By applying sufficient finger pressure, protuberance 18 effectively compresses and collapses hub 11 into bore 12 to occlude the bore and thereby restrict and prevent blood or other fluids from passing therethrough. In this manner, protuberance 18 acts as a shut-off valve controllable by the pressure applied to the folded wing 14 against hub 11 and wing 15. Various latching or locking devices may be employed with wings 14 and 15 to maintain them in the folded position while also restricting the flow of fluids through the bore; hooks, handles, friction devices and the like may be conveniently employed.

Once needle 21 has been withdrawn, the user may attach an infusion set for delivery of intravenous solution to the patient. The connection is made to the bore of hub 11 at the end opposite from catheter 20. As illustrated in FIG. 6, a tubing T is properly connected into bore 12 at end 25 of hub 11. At this time, wing 14 may be returned to its laterally extending position thereby removing the pinching pressure from hub 11; the intravenous solution is then allowed to flow from tube T through bore 12 and catheter 20 for delivery to the patient. Wings 14 and 15 may be secured to the body of the patient, for example, with adhesive strips S whereby the entire venipuncture and infusion set hook-up procedures are completed.

While many different materials may be selected to manufacture especially the hub and wing components, it is preferable to use a flexible plastic material such as polyvinyl chloride. For convenience of application, it is desirable to fabricate the intravenous catheter assembly of the present invention of sufficient size to allow it to fit, for instance, on the arm of a patient. Of course, the size of this catheter assembly is not critical, and may vary according to many factors.

Thus, the present invention provides an intravenous catheter assembly for use in the intravenous administration of fluids to a patient whereby the flow of fluids, either in or out of the assembly may be readily restricted by a convenient manipulation by its user to thereby provide an improvement over previously known and used catheter assemblies.

What is claimed is:

1. In combination, a needle having a sharp point at one of its ends and an intravenous catheter assembly, said catheter assembly comprising a flexible, compressible hub having a bore therethrough, a pair of generally oppositely extending flexible wing sections connected to said hub, one of said wing sections having a protuberance on one surface thereof aligned for contact with said hub when said wing section is folded over said hub, and a hollow catheter connected to said hub so that the lumen of said hollow catheter and said bore are in fluid communication, said needle slidably positioned in said bore and the lumen of said catheter so that said sharp point is adapted to extend out of a distal end of said catheter, said flexible wing sections adapted to fold toward each other so that said protuberance contacts said hub to cause said hub to compress in tight contact against said needle and thereby prevent relative movement between said needle and said catheter, said hub compression being the only means in said combination for preventing relative movement between said needle and said catheter.

* * * * *